US006618135B2

(12) United States Patent
Ichikawa (10) Patent No.: US 6,618,135 B2
(45) Date of Patent: Sep. 9, 2003

(54) LASER BEAM INSPECTION APPARATUS (75) Inventor: Iwao Ichikawa, Nishinomiya (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/726,596

(22) Filed: Dec. 1, 2000

(65) Prior Publication Data

US 2001/0002861 A1 Jun. 7, 2001

(30) Foreign Application Priority Data

Dec. 3, 1999 (JP) .......................... 11-344482
Oct. 26, 2000 (JP) ........................ 2000-326605

(51) Int. Cl.[7] ................................................ G01J 3/28
(52) U.S. Cl. ................................. 356/237.5; 356/236
(58) Field of Search ...................... 356/4, 403, 237.5, 356/316, 318, 319, 326, 323, 1; 349/10, 95, 114, 518, 104, 105, 106, 62, 67

(56) References Cited

U.S. PATENT DOCUMENTS

| 4,240,750 | A |   | 12/1980 | Kurtz et al. |  |
|---|---|---|---|---|---|
| 4,796,997 | A | * | 1/1989 | Svetkoff et al. | 356/4.06 |
| 4,963,017 | A | * | 10/1990 | Schneiter et al. | 356/3.01 |
| 5,020,901 | A | * | 6/1991 | de Groot | 356/498 |
| 5,082,362 | A | * | 1/1992 | Schneiter | 356/30.3 |
| 5,192,983 | A |   | 3/1993 | Tokura |  |
| 5,483,337 | A | * | 1/1996 | Barnard et al. | 356/316 |
| 5,798,805 | A | * | 8/1998 | Ooi et al. | 349/10 |
| 2001/0002861 | A1 | * | 6/2001 | Ichikawa | 356/237.1 |

OTHER PUBLICATIONS

Ryu, R.K. and H.S. Cho, "Visual Inspection Scheme for Use in Optical Solder Joint Inspection System," *Robotics and Automation*, 1996. Proceedings, 1996 IEEE International Conference in Minneapolis, Minnesota USA. Apr. 22–28, 1996, New York, NY, IEEE, Apr. 22, 1996, pp. 3259–3264. XP010163233.

* cited by examiner

Primary Examiner—Thien M. Le
(74) Attorney, Agent, or Firm—McDermott, Will & Emery (57) ABSTRACT A laser beams inspection apparatus suitable for inspecting electronic components such as ICs mounted on a substrate. The inspection apparatus includes a scan mechanism. The scan mechanism works to move a laser beam emitted from a laser emitter to scan a target one of electronic components in a given scan range. The scan mechanism is designed to change orientation of emission of the laser beam to change the scan range as a function of the type (e.g., the size) of the target electronic component, thereby minimizing inspection errors regardless of the type of the electronic components to be inspected.

17 Claims, 8 Drawing Sheets

LASER BEAM INSPECTION APPARATUS

BACKGROUND OF THE INVENTION

1. Technical Field of the Invention

The present invention relates generally to a laser beam inspection apparatus which inspects an electronic parts-fabricated substrate for defects, and more particularly to a laser beam inspection apparatus designed to monitor whether electronic parts or components are mounted in desired positions on a substrate or not and whether they are correct ones or not.

2. Background Art

Typical inspection apparatuses of the above type include a laser emitter radiating a laser beam onto each electronic component such as an IC mounted on a substrate, a laser receiver receiving a return of the laser beam from the electronic component, and an inspection circuit processing the return of the laser beam to obtain information about the appearance of the electronic component. Specifically, the inspection apparatuses of this type are designed to obtain the appearance information on the electronic components using the triangulation.

The above inspection apparatuses, however, have the drawback in that an inspection error may arise when the size of the electronic components is changed.

Specifically, the inspection apparatus first fixes a scan range in which a laser beam is to be radiated onto the substrate and then scans the laser beam in the scan range to determine the size of a target one of the electronic components and whether the target electronic component is mounted in a correct orientation or not. Therefore, in a case where a larger electronic component is inspected in the scan range which was determined when a smaller electronic component was inspected in a previous cycle, it may become impossible to scan the whole of an area of the larger electronic component including the tolerance, which leads to the inspection error.

Conversely, in a case where a smaller electronic component is inspected in the scan range which was determined when a larger electronic circuit component was inspected, it will cause the number of inspection points on the smaller electronic component to be decreased, thus resulting in an increase in resolution or a decrease in inspection accuracy.

SUMMARY OF THE INVENTION

It is therefore a principal object of the present invention to avoid the disadvantages of the prior art.

It is another object of the invention to provide an inspection apparatus capable of changing orientation of a scan of a laser beam and/or an area of a scan range as a function of the type of a target object to be inspected.

According to one aspect of the invention, there is provided an inspection apparatus which comprises: (a) a laser emitter emitting a laser beam for inspecting objects; (b) a scan mechanism moving the laser beam emitted from the laser emitter to scan a target one of the objects in a given scan range, the scan mechanism being designed to change orientation of emission of the laser beam to change the scan range; and (c) a laser receiver receiving a return of the laser beam from the target object to provide an object-inspected data.

In the preferred mode of the invention, the scan mechanism includes refracting members arranged adjacent each other along an optical path of the laser beam emitted from the laser emitter.

The refracting members may be made of flat plates.

The scan mechanism works to rotate the refracting members in the same direction about a given axis of rotation to achieve circular scanning of the laser beam.

The scan mechanism holds a given relative angle between the refracting members and rotates the refracting members to achieve the circular scanning of the laser beam in the scan range.

The scan mechanism includes an angle changing mechanism designed to change the relative angle between the refracting members to change the scan range and rotates the refracting members while keeping the relative angle to achieve the circular scanning of the laser beam in the changed scan range.

The angle changing mechanism changes a speed of rotation of one of the refracting members to change the scan range.

A moving mechanism is further provided which is designed to move the inspection apparatus from one of the objects to another having a different size after completion of a scan of the one of the objects. The angle changing mechanism changes the relative angle between the refracting members during movement of the inspection apparatus.

The scan mechanism may rotate the refracting members in opposite directions synchronously about the given axis of rotation to achieve rectilinear scanning of the laser beam in which a spot of the laser beam moves along a straight scan path.

The angle changing mechanism changes the relative angle between the refracting members to change orientation of the rectilinear scanning.

The objects to be inspected may be electronic components each made up of a body and a lead extending from the body. In this case, the scan mechanism rotates the refracting members made up of flat plates in the same direction synchronously about the given axis of rotation to achieve the circular scanning of the laser beam when the body of each of the electronic components is inspected. The angle changing mechanism changes and keeps the relative angle between the refracting members at 180° to achieve movement of the laser beam linearly when the lead is inspected.

The angle changing mechanism may change and rotate the refracting members in the opposite directions synchronously while keeping the relative angle between the refracting members at a given value to perform the rectilinear scanning of the laser beam when the lead is inspected.

According to another aspect of the invention, there is provided an inspection apparatus which comprises: (a) a laser emitter emitting a laser beam for inspecting objects; (b) a scan mechanism subjecting the laser beam emitted from the laser emitter to circular motion to scan a target one of the objects in a circular scan range cyclically, the scan mechanism being designed to control orientation of emission of the laser beam to determine an area of the circular scan range as a function of the size of the target object; and (c) a laser receiver receiving a return of the laser beam from the target object to provide an object-inspected data.

According to the third aspect of the invention, there is provided an inspection apparatus which comprises: (a) a laser emitter emitting a laser beam for inspecting objects; (b) a scan mechanism including refracting members disposed adjacent to each other along an optical path of the laser beam to change orientation of emission of the laser beam emitted from the laser emitter to perform rectilinear scanning about a target one of the objects, the scan mechanism being designed to change a relative angle between the refracting members to change orientation of the rectilinear scanning of the laser beam as a function of orientation of the target object; and (c) a laser receiver receiving a return of the laser beam from the target object to provide an object-inspected data.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
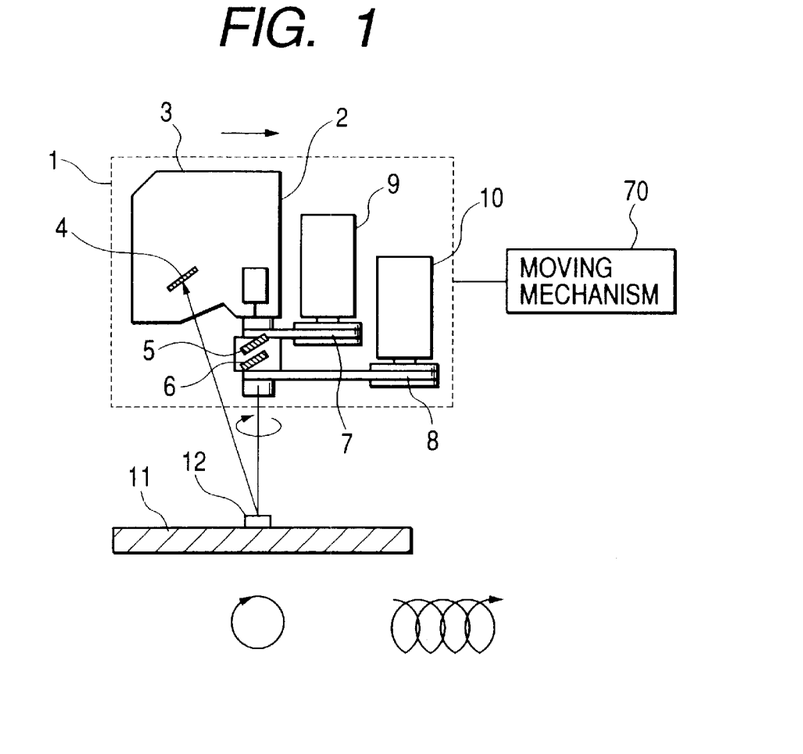
FIG. 1 is a partially sectional view which shows an inspection apparatus according to the invention.

Referring to the drawings, wherein like reference numbers refer to like parts in several views, particularly to FIG. 1, there is shown a laser beam inspection apparatus according to the present invention which is designed to monitor whether electronic components are each mounted in a desired position on a substrate or not and whether they are correct ones or not.

The inspection apparatus includes a body 1, a sensor head 2, a set of flat glass plates 5 and 6 (i.e., refracting members), servomotors 9 and 10, and a moving mechanism 70.

The sensor head 2 has disposed therein a laser emitter 3 and a laser receiver 4. The glass plates 5 and 6 are disposed beneath the laser head 2 and arranged adjacent each other at a given interval along an optical path of a laser beam emitted from the laser emitter 3. The glass plates 5 and 6 are supported by the body 1 rotatably and connected to the servomotors 9 and 10 through timing belts 7 and 8, respectively. The moving mechanism 70 includes, for example, an XY table designed to move the body 1 horizontally and vertically on a plane.

Figure 3:
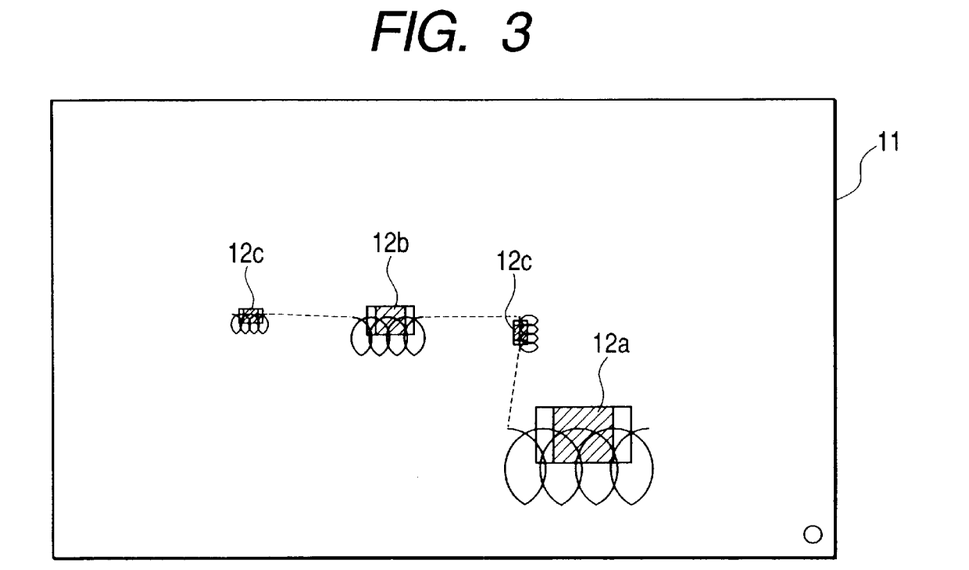
FIG. 3 is a plan view which shows a scan path of a laser beam for inspecting electronic components having different sizes.

Placed beneath the inspection apparatus is a substrate 11 on which a plurality of circuit components 12 are mounted. FIG. 3 shows an example of electronic components mounted on the substrate 11. The electronic component 12a is the largest in size. The electronic component 12b is the second largest. The electronic component 12d is the smallest.

Figure 2:
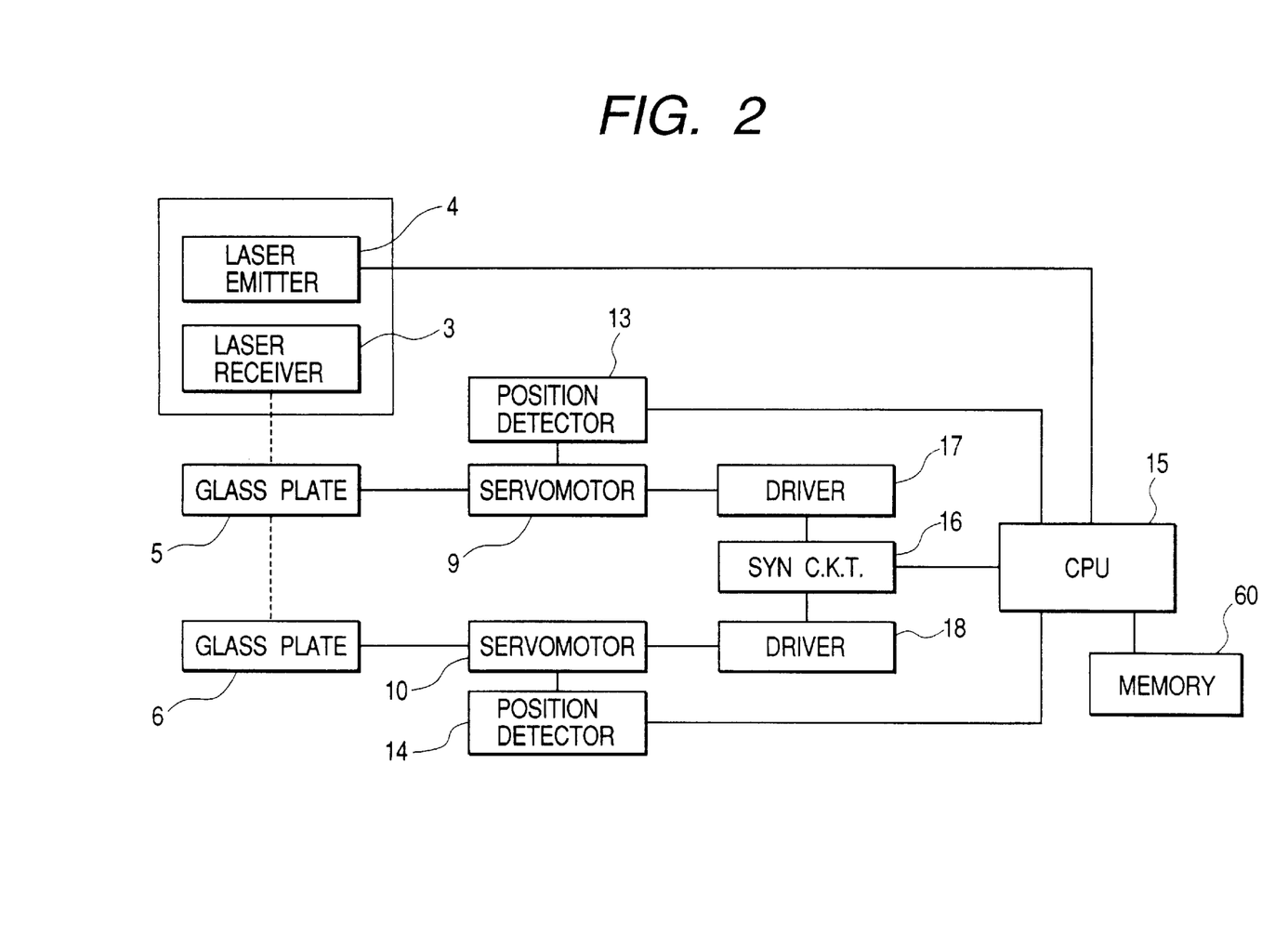
FIG. 2 is a circuit diagram which shows a circuit structure of the inspection apparatus of FIG. 1.

FIG. 2 shows a circuit structure of the inspection apparatus.

The servomotors 9 and 10 are coupled with position detectors (e.g., encoders) 13 and 14, respectively. The laser emitter 3 includes, for example, a semiconductor laser. The laser receiver 4 includes, for example, a light-sensitive element. The laser receiver 4 and the position detectors 13 and 14 are coupled with a CPU 15. Specifically, the position detectors 13 and 14 monitor angular positions of the servomotors 9 and 10 and output position signals indicative thereof to the CPU 15, respectively.

Figure 4A:
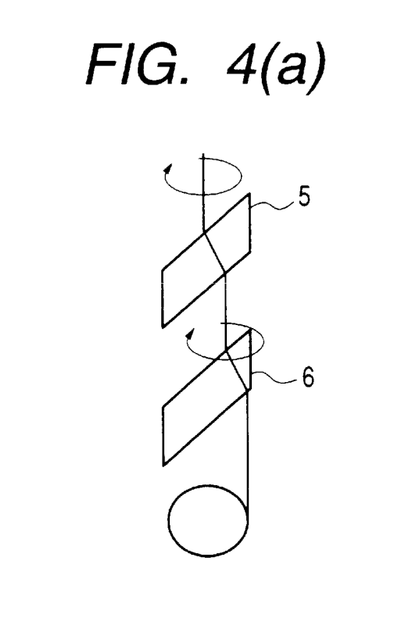
FIGS. 4(a), 4(b), and 4(c) are side views which show a pair of refracting members built in the inspection apparatus of FIG. 1 which are designed to change an area of a scan range as a function of a relative angle therebetween.
Figure 4B:
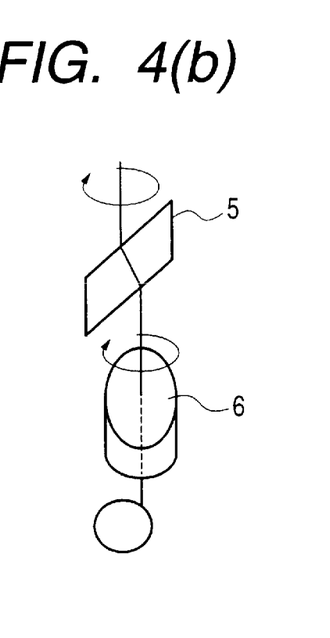
Figure 4C:
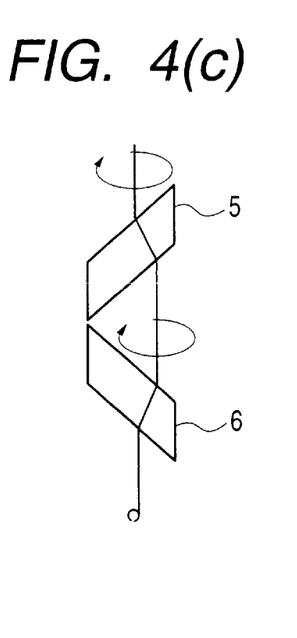

The servomotors 9 and 10 are, as described above, connected to the glass plates 5 and 6 through the timing belts 9 and 10 and to motor drivers 17 and 18, respectively. The motor drivers 17 and 18 usually rotate the servomotors 9 and 10 synchronously through a synchronization circuit 16, but either of the motor drivers 17 and 18 is controlled by the CPU 15 to change the speed of a corresponding one of the servomotors 9 and 10 temporarily to establish, as shown in FIGS. 4(a), 4(b), and 4(c), three angular relations between the glass plates 5 and 6. Specifically, the CPU 15 provides a synchronization disable signal to the synchronization circuit 16 to disable the synchronization of the servomotors 9 and 10 and increases or decreases the speed of one of the glass plates 5 and 6 to establish a desired angular relation between the glass plates 5 and 6.

FIG. 4(a) illustrates for the case where surfaces of the glass plates 5 and 6 are in parallel to each other, which will be referred to below as a relative angle of zero (0°). By rotating the glass plates 5 and 6 synchronously through the servomotors 9 and 10 while keeping the relative angle of 0°, a laser beam emitted from the laser emitter 3 scans, as shown in the lower side of FIG. 4(a), along a larger circle.

Figure 4D:
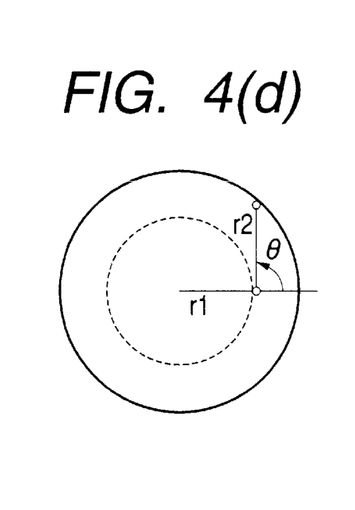
FIG. 4(d) shows a scan locus of a laser beam in the case of FIG. 4(b)

FIG. 4(b) illustrates for the case where the surfaces of the glass plates 5 and 6 are oriented in different directions at a relative angle of 90°. FIG. 4(d) shows a scan locus of a laser beam in the case of FIG. 4(b). r1 indicates the radius of a rotational path of the glass plate 5. r2 indicates the radius of a rotational path of the glass plate 6. θ indicated the relative angle between the glass plates 5 and 6. A solid line indicates a scan locus of a laser beam passing through the glass plates 5 and 6. Specifically, by rotating the glass plates 5 and 6 synchronously through the servomotors 9 and 10 while keeping the relative angle of 90°, a laser beam emitted from the laser emitter 3 scans, as shown in the lower side of FIG. 4(*b*), along a circle smaller than the one shown in FIG. 4(*a*).

FIG. 4(*c*) illustrates for the case where the glass plates 5 and 6 are oriented in opposite directions at a relative angle of 180°. This positional relation is achieved by disenabling the synchronization circuit 16, changing one of the glass plates 5 and 6, and stopping the one of the glass plates 5 and 6 after it have rotated 90° from the status of FIG. 4(*b*) or 180° from the status of FIG. 4(*a*). By rotating the glass plates 5 and 6 synchronously through the servomotors 9 and 10 while keeping the relative angle of 180°, a laser beam emitted from the laser emitter 3 forms a spot, as shown in the lower side of FIG. 4(*c*).

Figure 5A:
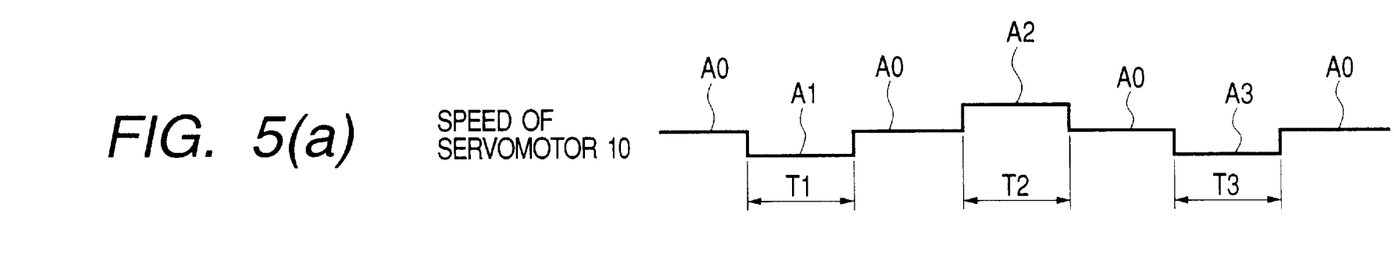
FIGS. 5(a) and 5(b) are time charts which show a speed difference between servomotors for changing the relative angle between the refracting members as shown in FIGS. 4(a) to 4(c)
Figure 5B:
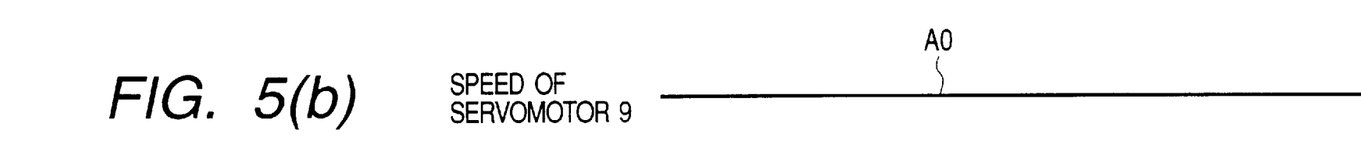
Figure 5C:
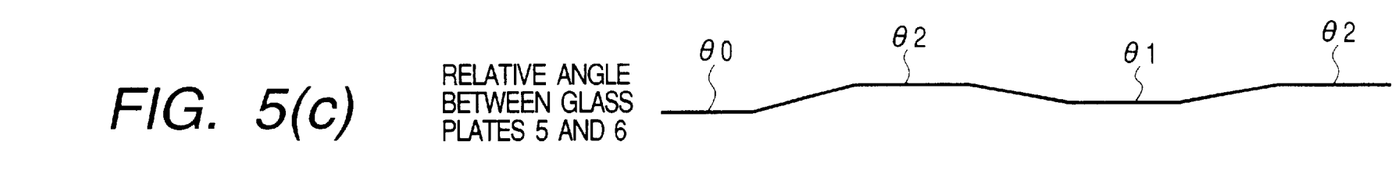
FIG. 5(c) is a time chart which shows a relative angle between the refracting members defined by the speed difference of the servomotors as shown in FIGS. 5(a) and 5(b)

FIGS. 5(*a*), 5(*b*), and 5(*c*) show one example of a relation between speed control of the servomotors 10 and 9 and the relative angle between the glass plates 5 and 6. Assume that the servomotors 10 and 9 are first controlled by the motor drivers 18 and 17 so that they rotate at the same speed A0 with the glass plates 5 and 6 oriented at a relative angle θ0 of 0°. When it is required to establish a relative angle of 180° between the glass plates 5 and 6, the motor driver 18 decreases the speed of the servomotor 10 to rotate the servomotor 10 at a speed A1 for a time period of T1 until a relative angle θ2 of 180° is reached and then returns the speed of the servomotor 10 to A0. Next, when it is required to establish a relative angle of 90° between the glass plates 5 and 6, the motor driver 18 increases the speed of the servomotor 10 to rotate the servomotor 10 at a speed of A2 for a time period of T2 until a relative angle θ1 of 90° is reached and then returns the speed of the servomotor 10 back to A0. Subsequently, when it is required to return the relative angle θ1 to the relative angle θ2, the motor driver 18 decreases the speed of the servomotor 10 to rotate the servomotor 10 at a speed A3 for a time period of T3 until a relative angle θ2 of 180° is reached and then returns the speed of the servomotor 10 to A0.

Note that the time periods T1, T2, and T3 may either be equal to or different from each other. In a case where the time periods T1, T2, and T3 are set equal to each other, the speeds A1, A2, and A3 of the servomotor 10 may be changed to establish desired relative angles between the glass plates 5 and 6, respectively. Conversely, in a case where the speeds A1, A2, and A3 are kept constant, the time periods T1, T2, and T3 may be set different from each other. Specifically, the CPU 15 may control the speed of either or both of the servomotors 9 and 10 to change the angle between the glass plates 5 and 6 to a desired one, thereby modifying an area of a scan range of a laser beam emitted from the sensor head 2.

When the inspection apparatus is moved to the right, as viewed in FIG. 1, by the moving mechanism 70 while keeping the relative angle between the glass plates 5 and 6 at a desired one, it will cause a laser beam to travel to the right, as shown in a lower side of the drawing, while scanning the surface of the substrate 11 along circles of a desired size.

When it is required to inspect the electronic components 12*a* to 12*c* on the substrate 11, as shown in FIG. 3, the CPU 15 moves the inspection apparatus horizontally and rotates the servomotors 9 and 10 synchronously at the same speed while keeping the relative angle between the glass plates 5 and 6 at zero (0°), thereby causing a laser beam to scan the largest electronic component 12*a* along the largest circles. After completion of a given number of circular scan cycles of the electronic component 12*a*, the CPU 15 confirms the location and size of the electronic component 12*c* to be inspected next by look-up using data stored in the memory 60 installed in the inspection apparatus and adjusts the relative angle between the glass plates 5 and 6 to, for example, 160° to change the scan range to one predetermined as a function of the size of the electronic component 12*c*. The CPU 15 moves the inspection apparatus upward to the electronic component 12*c* through the moving mechanism 70 and starts a scan of the electronic component 12*c* in the smallest scan range. The adjustment of the relative angle between the glass plates 5 and 6 may be made during movement of the inspection apparatus to the electronic component 12*c*. After completion of a given number of circular scans of the electronic component 12*c*, the CPU 15 confirms the location and size of the electronic component 12*b* to be inspected next by look-up using data stored in the memory and adjusts the relative angle between the glass plates 5 and 6 to, for example, 100° to change the scan range to one predetermined as a function of the size of the electronic component 12*b*. The CPU 15 moves the inspection apparatus horizontally to the electronic component 12*b* through the moving mechanism 70 and starts a scan of the electronic component 12*b* in the middle sized-scan range. After completion of a given number of scans of the electronic component 12*b*, the CPU 15 confirms the location and size of the electronic component 12*c* to be inspected next by look-up using data stored in the memory and adjusts the relative angle between the glass plates 5 and 6 to 160° that is identical with that in the second scan. The CPU 15 then moves the inspection apparatus horizontally and starts a scan of the electronic component 12*c*.

The inspection apparatus of this embodiment is, as apparent from the above discussion, capable of changing the scan range as a function of the size of an electronic component to be inspected, thereby minimizing inspection errors. Specifically, in the example of FIG. 3, the electronic components 12*a* to 12*c* are different in size from each other and have different tolerances in mounting on the substrate 11. The optimum scan ranges for inspecting the electronic components 12*a* to 12*c* are, therefore, different in area from each other. If the largest electronic component 12*a* is scanned in the smallest scan range for the electronic component 12*c*, it may result in an error in detecting the presence of the electronic component 12*a*. Conversely, if the smallest electronic component 12*c* is scanned in the largest scan range, it will consume time more than required, thus resulting in an increase in total time for inspection of the electronic components 12*a* to 12*c*.

Figure 6:
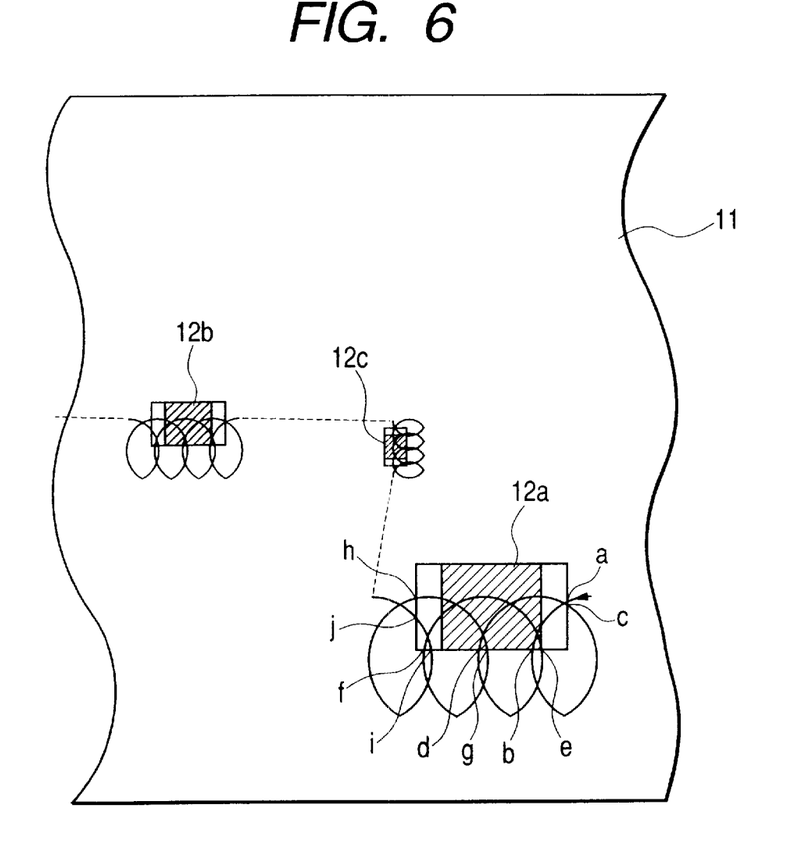
FIG. 6 is a partial view which shows a scan path of a laser beam in circular scanning performed by the inspection apparatus of FIG. 1.

In the example shown in FIG. 3, the laser beam scans each of the electronic components 12*a* to 12*c* four cycles regardless of the size of the electronic components 12*a* to 12*c*. Taking as an example the largest electronic component 12*a*, the laser beam, as shown in FIG. 6, first runs on the electronic component 12*a* from the substrate 11 at point a and then drops to the substrate at point b. Next, the laser beam runs on the electronic component 12*a* again at point c and drops to the substrate 11 at point d. Such a scan cycle is further repeated two times. The laser beam last drops to the substrate 11 from the electronic component 12*a* at point j. Specifically, four scans are performed to sample ten data on the electronic component 12*a*. The laser receiver 4 receives and converts a return of the laser beam from the substrate 11 into an electric signal and outputs it to the CPU 15. The CPU 15 picks up the sampled data from the signal outputted from the laser receiver 4 and compares them with reference data stored in the memory 60 to determine, for example, the size and orientation of the electronic component 12a, thereby determining whether the electronic component 12a is mounted on the substrate 11 in a correct position or not and whether the electronic component 12a is a desired one or not.

Figure 7:
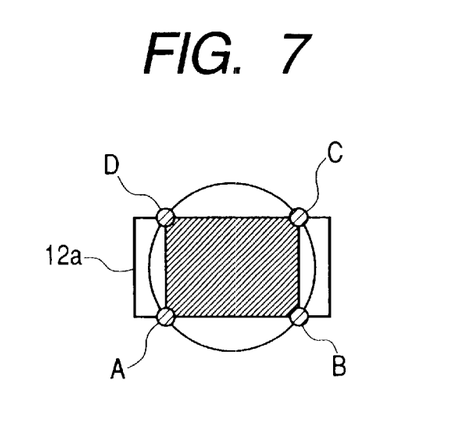
FIG. 7 is an illustration which shows a scan path of a laser beam in a modification of the inspection apparatus of FIG. 1.

FIG. 7 shows a modification of the above first embodiment.

In operation, the inspection apparatus first moves to the electronic component 12a on the substrate 11 and stops above it. The laser emitter 3 radiates a laser beam to scan the electronic component 12a only one cycle. Specifically, the glass plates 5 and 6 are turned one cycle in the angular relation as shown in FIG. 4(a). The scanning of the electronic component 12a in a circular range whose radius is smaller than the length of the electronic component 12a enables four data on the electronic component 12a to be sampled at points A, B, C, and D. This results in decrease in accuracy of the inspection, but allows the time required to inspect each electronic component to be decreased as compared with the above embodiment. This modification is, thus, applicable to the case where the mounting accuracy is not so critical.

Figure 8:
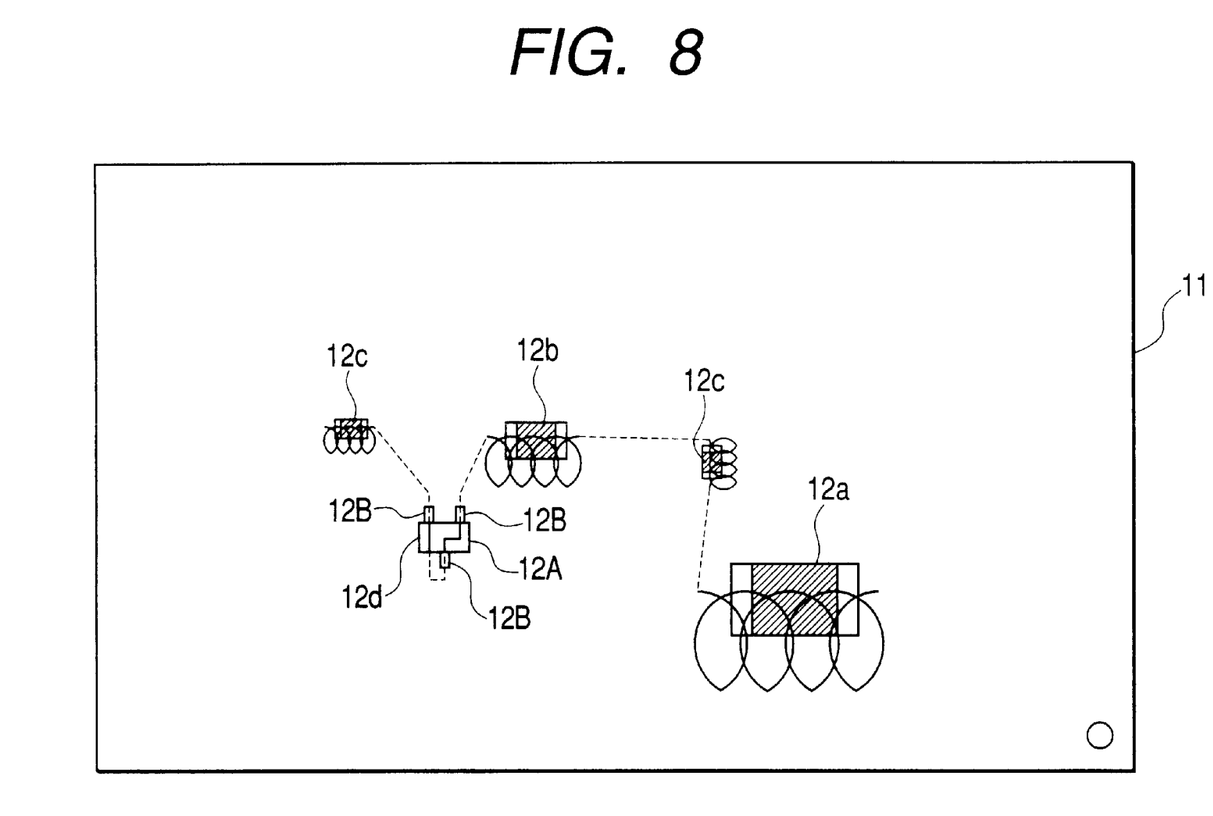
FIG. 8 is a plan view which shows a scan path of a laser beam for inspecting lead pins installed on an electronic component.

FIG. 8 illustrates a scan path of the laser beam in a case where it is required to check whether three terminal pins 12B of an electronic component 12d are mounted on the substrate 11 correctly or not as well as inspecting the electronic components 12a to 12c mounted on the substrate 11. The terminal pins 12B project outward from a body 12A of the electronic component 12d.

In operation, after completion of a scan of the electronic component 12b, the CPU 15 adjusts the relative angle between the glass plates 5 and 6 to 180°, as shown in FIG. 4(c), to change the circular scan range to a spot one and moves the laser beam along a broken line, as indicated in FIG. 8, scan the three terminal pins 12B. This enables the inspection of small parts without stopping the rotation of the glass plates 5 and 6 or changing the relative angle therebetween to decrease the scan range.

The inspection apparatus may alternatively rotate the glass plates 5 and 6 in opposite directions in the above embodiments to achieve rectilinear scanning in which the laser beam moves along a straight scan path, thereby allowing leads of small electronic parts such as ICs, which are difficult to detect with the circular scanning, to be inspected at high speeds.

The above rectilinear scanning technique will be described below in detail with reference to FIGS. 9(a) to 11.

Figure 9A:
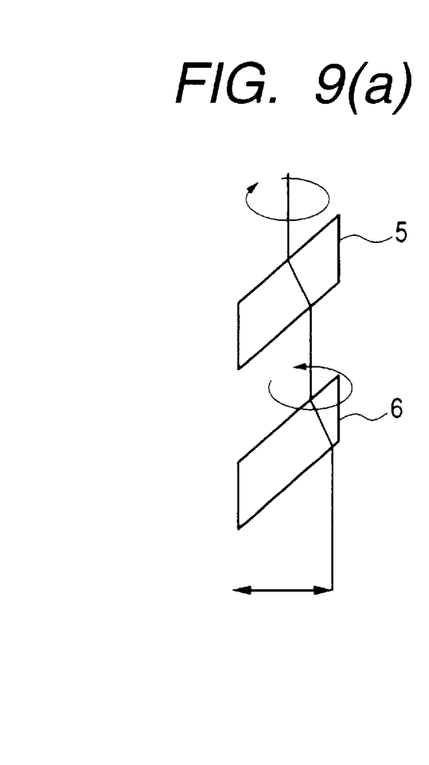
FIGS. 9(a), 9(b), and 9(c) are side views which show a pair of refracting members built in the inspection apparatus of FIG. 1 which are designed to change orientation of a scan of a laser beam in rectilinear scanning.

FIG. 9(a) illustrates the glass plates 5 and 6 which are held at a relative angle of zero (0°). Rotating the glass plates 5 and 6 synchronously in opposite directions causes a laser beam emitted from the laser emitter 3 to move along a straight scan path, as indicated by A in FIG. 9(d), extending horizontally, as viewed in the drawing.

Figures 9B, 9C:
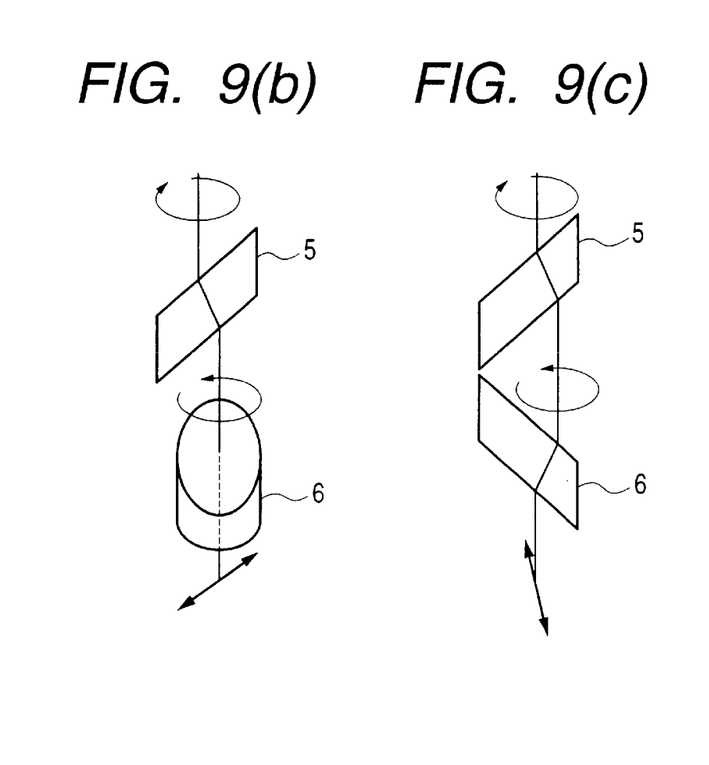
Figure 9D:
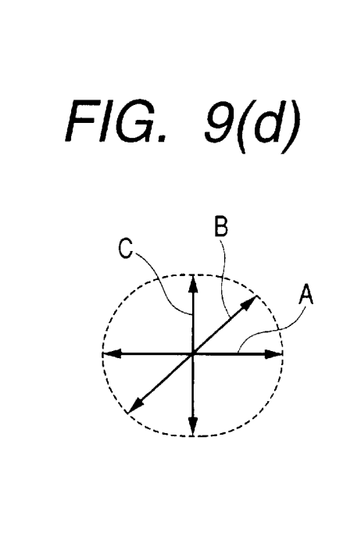
FIG. 9(d) is a plan view which shows the orientation of the scan of the laser beam defined by a relative angle between the refracting members as shown in each of FIGS. 9(a) to 9(c)

FIG. 9(b) illustrates the glass plates 5 and 6 which are held at a relative angle of 90°. Rotating the glass plates 5 and 6 synchronously in opposite directions causes a laser beam emitted from the laser emitter 3 to move along a straight scan path, as indicated by B in FIG. 9(d), extending at 45° to the scan path A.

FIG. 9(c) illustrates the glass plates 5 and 6 which are held at a relative angle of 180°. Rotating the glass plates 5 and 6 synchronously in opposite directions causes a laser beam emitted from the laser emitter 3 to move along a straight scan path, as indicated by C in FIG. 9(d), extending at 90° to the scan path A.

Figure 10:
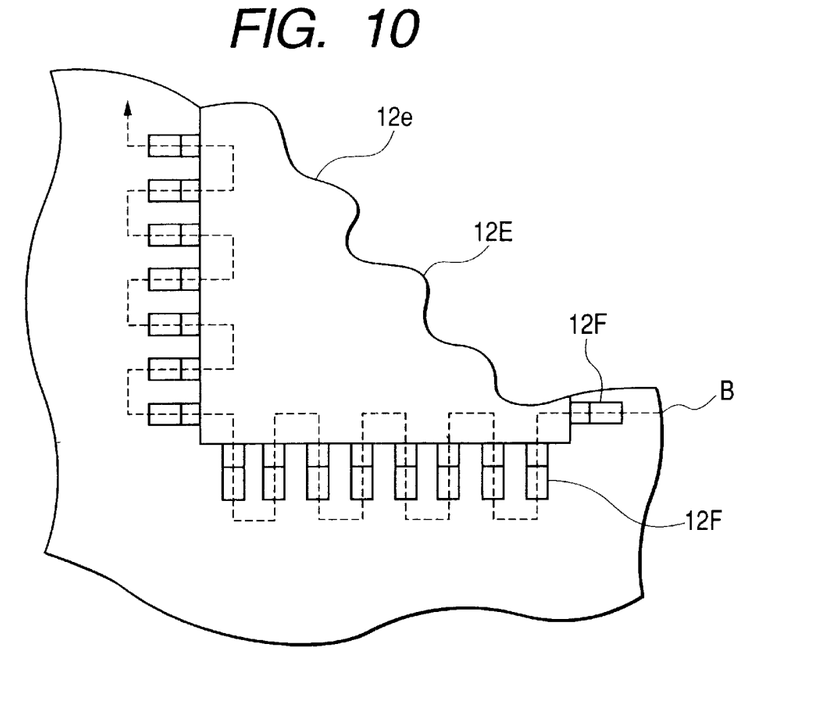
FIG. 10 is an illustration which shows a scan path of a laser beam when lead pins installed on a IC are inspected in rectilinear scanning.

FIG. 10 shows an example of inspecting electronic components mounted on the substrate 11 with the above described straight scanning.

The substrate 11 has disposed thereon a plurality of ICs 12e (one is shown for the brevity of illustration) The IC 12e has a plurality of leads 12F extending outward from the periphery of a body 12E.

In operation, the moving mechanism 70 moves the body 1 of the inspection apparatus around the IC 12e along a broken line A as shown in FIG. 10. First, the moving mechanism 70 stops the body 1 above one of the leads 12F which extends horizontally as viewed in the drawing. Next, the CPU 15 adjusts the relative angle between the glass plate 5 and 6 to zero (0°), as shown in FIG. 9(a), and rotates the glass plates 5 and 6 synchronously in opposite directions, thereby causing the laser beam to move horizontally along the scan path A shown in FIG. 9(d). Specifically, the laser beam traverses the length of the lead 12e, thus allowing the CPU 15 to determine whether the lead 12F is mounted on the substrate 11 in a correct position or not.

After completion of the scan of the lowermost one of the right array of the leads 12F, as viewed in FIG. 10, the moving mechanism 70 moves the body 1 to a rightmost one of the lower array of the leads 12F and stops above it. The CPU 15 adjusts the relative angle between the glass plate 5 and 6 to 180°, as shown in FIG. 9(c), and rotates the glass plates 5 and 6 synchronously in opposite directions, thereby causing the laser beam to move vertically along the scan path C shown in FIG. 9(d). Specifically, the laser beam traverses the length of the lead 12F, thus allowing the CPU 15 to determine whether the lead 12F is mounted on the substrate 11 in a correct position or not.

Figure 11:
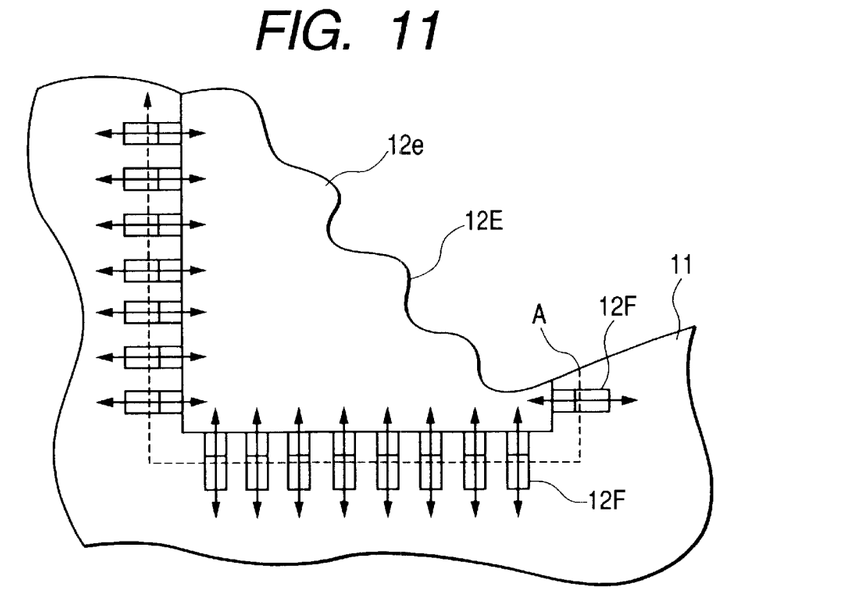
FIG. 11 is a comparative example of inspecting leads through circular scanning where refracting members are held at a relative angle of 180°.

FIG. 11 shows a comparative example of inspecting the leads 12F through the circular scanning where the glass plates 5 and 6 are held at a relative angle of 180°. In this case, complete inspection of all the leads 12F requires the laser beam to move along a zigzag broken line B, which results in an increase in total length of the scan path, thus leading to a reduction in inspection speed.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. An inspection apparatus comprising:
   a laser emitter emitting a laser beam for inspecting objects;
   a scan mechanism moving the laser beam emitted from said laser emitter to scan a target one of the objects in a given scan range, said scan mechanism being designed to change orientation of emission of the laser beam to change the scan range; and
   a laser receiver receiving a return of the laser beam from the target object to provide an object-inspected data, wherein
   said scan mechanism includes refracting members arranged adjacent each other along an optical path of the laser beam emitted from said laser emitter.

2. An inspection apparatus as set forth in claim 1, wherein the refracting members are made of flat plates.

3. An inspection apparatus as set forth in claim 1, wherein said scan mechanism rotates the refracting members in the same direction about a given axis of rotation to achieve circular scanning of the laser beam.

4. An inspection apparatus as set forth in claim 3, wherein said scan mechanism holds a given relative angle between the refracting members and rotates the refracting members to achieve the circular scanning of the laser beam in the scan range.

5. An inspection apparatus as set forth in claim 4, wherein said scan mechanism includes an angle changing mechanism designed to change the relative angle between the refracting members to change the scan range and rotates the refracting members while keeping the relative angle to achieve the circular scanning of the laser beam in the changed scan range.

6. An inspection apparatus as set forth in claim 5, wherein said angle changing mechanism changes a speed of rotation of one of the refracting members to change the scan range.

7. An inspection apparatus as set forth in claim 5, further comprising a moving mechanism designed to move the inspection apparatus from one of the objects to another having a different size after completion of a scan of the one of the objects, and wherein said angle changing mechanism changes the relative angle between the refracting members during movement of the inspection apparatus.

8. An inspection apparatus as set forth in claim 1, wherein said scan mechanism rotates the refracting members in opposite directions synchronously about a given axis of rotation to achieve rectilinear scanning of the laser beam in which a spot of the laser beam moves along a straight scan path.

9. An inspection apparatus as set forth in claim 8, wherein said scan mechanism includes an angle changing mechanism designed to change the relative angle between the refracting members to change orientation of the rectilinear scanning.

10. An inspection apparatus as set forth in claim 9, wherein said angle changing mechanism changes a speed of rotation of one of the refracting members to change the relative angle between the refracting members.

11. An inspection apparatus as set forth in claim 10, further comprising a moving mechanism designed to move the inspection apparatus from one of the objects to another having a different size after completion of a scan of the one of the objects, and wherein said angle changing mechanism changes the relative angle between the refracting members during movement of the inspection apparatus.

12. An inspection apparatus as set forth in claim 5, wherein the objects to be inspected are electronic components each made up of a body and a lead extending from the body, and wherein said scan mechanism rotates the refracting members made up of flat plates in the same direction synchronously about the given axis of rotation to achieve the circular scanning of the laser beam when the body of each of the electronic components is inspected, and said angle changing mechanism changes and keeps the relative angle between the refracting members at 180° to achieve movement of the laser beam linearly when the lead is inspected.

13. An inspection apparatus as set forth in claim 12, further comprising a moving mechanism designed to move the inspection apparatus from one of the objects to another having a different size after completion of a scan of the one of the objects, and wherein said angle changing mechanism changes the relative angle between the refracting members during movement of the inspection apparatus.

14. An inspection apparatus as set forth in claim 9, wherein the objects to be inspected are electronic components each made up of a body and a lead extending from the body, and wherein said scan mechanism rotates the refracting members made up of flat plates synchronously in the same direction about the given axis of rotation to achieve circular scanning of the laser beam when the body of each of the electronic components is inspected, and said angle changing mechanism changes and rotates the refracting members in the opposite directions synchronously while keeping the relative angle between the refracting members at a given value to perform the rectilinear scanning of the laser beam when the lead is inspected.

15. An inspection apparatus as set forth in claim 14, further comprising a moving mechanism designed to move the inspection apparatus from one of the objects to another having a different size after completion of a scan of the one of the objects, and wherein said angle changing mechanism changes the relative angle between the refracting members during movement of the inspection apparatus.

16. An inspection apparatus comprising:
a laser emitter emitting a laser beam for inspecting objects;
a scan mechanism subjecting the laser beam emitted from said laser emitter to circular motion to scan a target one of the objects in a circular scan range cyclically, said scan mechanism being designed to control orientation of emission of the laser beam to determine an area of the circular scan range as a function of the size of the target object; and
a laser receiver receiving a return of the laser beam from the target object to provide an object-inspected data, wherein
said scan mechanism includes refracting members arranged adjacent each other along an optical path of the laser beam emitted from said laser emitter.

17. An inspection apparatus comprising:
a laser emitter emitting a laser beam for inspecting objects;
a scan mechanism including refracting members disposed adjacent to each other along an optical path of the laser beam to change orientation of emission of the laser beam emitted from said laser emitter to perform rectilinear scanning about a target one of the objects, said scan mechanism being designed to change a relative angle between the refracting members to change orientation of the rectilinear scanning of the laser beam as a function of orientation of the target object; and
a laser receiver receiving a return of the laser beam from the target object to provide an object-inspected data.

* * * * *